United States Patent [19]

Johanson

[11] 4,217,112
[45] Aug. 12, 1980

[54] PRODUCTION OF FUEL GAS BY LIQUID PHASE HYDROGENATION OF COAL

[75] Inventor: Edwin S. Johanson, Princeton, N.J.

[73] Assignee: Hydrocarbon Research, Inc., Lawrenceville, N.J.

[21] Appl. No.: 974,555

[22] Filed: Dec. 29, 1978

[51] Int. Cl.² ............................ C07C 1/00; C10G 1/06
[52] U.S. Cl. ................................... 48/210; 208/8 LE
[58] Field of Search .................. 48/197 R, 210, 214 A, 48/214 R; 208/8 LE; 252/373; 423/652

[56] References Cited

U.S. PATENT DOCUMENTS

| | | | |
|---|---|---|---|
| 2,813,779 | 11/1957 | Faatz | 423/652 |
| 3,617,465 | 11/1971 | Johanson et al. | 48/197 R |
| 3,769,198 | 10/1973 | Johanson et al. | 48/197 R |
| 3,836,344 | 9/1974 | Krawitz et al. | 48/214 R |
| 4,071,330 | 1/1978 | Sederquist | 423/652 |
| 4,115,075 | 9/1978 | McNamee et al. | 48/210 |

*Primary Examiner*—Peter F. Kratz
*Attorney, Agent, or Firm*—Michael A. Jacobs

[57] ABSTRACT

The thermal hydrogenation of solid coal without added catalyst produces hydrocarbon gases in the methane to propane range as the principal product, plus substantial yields of synthetic petroleum-like hydrocarbon liquids. The $C_4$-400° F. naphtha liquid fraction is steam reformed to produce hydrogen, while heavier distillate liquid fractions are used as fuel to operate the steam reformer and for other process heat requirements, so that all of the hydrogen required for the coal hydrogenation reaction is produced from portions of the liquid products.

22 Claims, 2 Drawing Figures

PRODUCTION OF FUEL GAS BY LIQUID PHASE HYDROGENATION OF COAL

BACKGROUND OF THE INVENTION

1. Field of the Invention

This invention pertains to the thermal hydrogenation of coal to produce principally fuel gas product. It pertains more particularly to an integrated coal hydrogenation process without added catalyst for producing $C_1$–$C_3$ boiling range fuel gases, wherein essentially all the $C_4$–400° F. light liquid fractions produced are steam reformed to make the needed hydrogen, and the heavier 400°–975° F. liquid fractions are used as fuel for the reformer and other process needs.

2. Description of Prior Art

It has been determined that one of the most costly factors in the thermal hydrogenation of solid coal with the objective of mainly producing normally gasiform hydrocarbons is the cost of hydrogen. Consumption of hydrogen varies somewhat with the rank of the coal, but usually amounts to from 10 to 20 standard cubic feet (SCF) per pound of coal feed. There must be a source of relatively high purity hydrogen readily available to the hydrogenation reactor, and supplying the required hydrogen has posed a problem. An economic and technically advanced process for production of hydrogen is that of steam reforming of low boiling hydrocarbon liquids, and a coal hydrogenation process producing mainly fuel gas product while also supplying these constituents in sufficient quantity from the coal for making needed hydrogen would provide important economic advantages.

While the hydrogenation of coal without added catalyst to produce gaseous and liquid products is known, having been disclosed in U.S. Pat. No. 3,617,465 to Wolk et al., such processes have produced principally coal-derived liquids along with only incidental amounts of gas. Also, such processes have used externally produced hydrogen for make-up requirements and have not provided internally a convenient source of the needed make-up hydrogen of desired or optimum purity, while also producing principally a fuel gas product having high heating value.

SUMMARY OF THE INVENTION

This invention discloses an integrated coal hydrogenation process not requiring added catalyst for producing principally methane through propane fuel gas product, plus sufficient hydrocarbon liquids that are used in the production of the necessary hydrogen via steam reforming for both the chemical feed and the fuel requirements. This process for hydrogenation of particulate coal solids in a liquid phase coal hydroconversion reaction without added catalyst to produce mainly $C_1$–$C_3$ fuel gas product is materially increased in overall efficiency and reduced in cost by the utilization of a naphtha boiling range fraction of reactor liquid effluent, preferably $C_4$–400° F., as the source of hydrocarbons for reforming with steam to make the hydrogen needed, combined with the utilization of fuel oil boiling range distillate liquid, preferably 400°–975° F., as the fuel source for the reformer furnace. Such steam reforming of naphtha to produce the hydrogen needed in the process is advantageous over partial oxidation gasification of heavy liquid residue material from coal hydrogenation, followed by reforming to produce the needed hydrogen.

A further advantage of this coal hydrogenation process is its product flexibility, so that whenever the demand for fuel gas product is low the production of fuel gas can be reduced and the production of distillate liquid product correspondingly increased, so as to maintain substantially the same coal feed rate and thereby fully utilize the plant capacity. Specifically, the process provides sufficient flexibility to respond to seasonal product demands, i.e. when the demand for fuel gas product is reduced, the reaction conditions are selected so as to produce less gas along with some excess distillate liquid, and to provide some net liquid product after the chemical feed and fuel needs for the reforming step to produce the required hydrogen have been met.

A relationship exists between the severity of the hydrogenation reaction and the product distribution provided. By increasing the severity of the hydrogenation reaction, such as by either increasing the reaction zone temperature or reducing the coal space velocity or both, the percentage of $C_1$–$C_3$ gas product can be increased, but only up to a limit. Such limitation is placed upon the percent gas produced and upon the useful reactor operating conditions by the need also to produce sufficient $C_4$–400° F. naphtha for feed along with steam to the reformer and to produce sufficient 400°–975° F. distillate liquid to fuel the reformer, so as to provide the fresh hydrogen required in the coal hydrogenation reaction step.

The process of this invention is useful at reaction zone conditions within the broad range of about 840°–920° F. temperature, 1000–3000 psig hydrogen partial pressure, and coal throughput or space velocity rates of about 5–50 pounds per hour per cubic foot of reaction space, at which conditions both fuel gas and net distillate liquid products are made.

The operation of this process for predominately gas production is at reaction zone conditions of 865°–880° F. temperature, 1750–2800 psig hydrogen partial pressure, and 10–30 lbs coal/hr/ft$^3$ space velocity, where the methane through propane gas production amounts to at least about 14 weight percent of the coal feed, and usually 20–40 weight percent, preferably 35–40 weight percent, along with approximately equal quantities of $C_4$–400° F. naphtha and of 400°–975° F. distillate liquid products. The $C_4$–400° F. naphtha and distillate liquid products are used to manufacture the hydrogen consumed in the reaction zone. The operation of the process with slight modification of conditions for joint production of mainly methane through propane gas product and some net liquid products is at reaction zone conditions of 850°–865° F. temperature, 1700–2600 psig hydrogen partial pressure, and 15–40 lbs coal/hr/ft$^3$ space velocity, where the methane through propane gas yield is 10–25 weight percent of coal feed, and the reactor yield of naphtha and heavy distillate liquids amount to about 55 weight percent of coal feed. After meeting the hydrogen and fuel requirements of the process by converting the naphtha to hydrogen and using a portion of the fuel oil for the heat requirements, this leaves a net plant yield of distillate oil liquids up to 20 weight percent of the coal feed. The preferred embodiment of this invention is for producing maximum gas product, at which conditions the thermal value of the gas product is about 65–70% of that of the coal fed, while all of the naphtha and heavy distillate liquid products made in the coal hydrogenation reaction are consumed in the steam reforming step to produce hydrogen.

It is usually desirable for process control purposes to produce and feed to the steam reformer naphtha in excess of that needed to produce the hydrogen required. The reformer is conveniently operated in a low temperature range of 1450°–1750° F. to make a hydrogen-methane gas mixture, as the methane thus formed represents additional fuel gas product. Thus, it is also an advantage of this invention that the steam reformer can be satisfactorily operated at reduced temperature conditions and thus require less fuel to produce the hydrogen-methane gas mixture. Such a hydrogen-methane gas mixture can be conveniently used directly without extensive purification other than the usual $CO_2$ removal as the make-up hydrogen required in the hydrogenation reaction step, because the methane fraction contributes to producing additional $C_1$–$C_3$ fuel gas product. Thus, while the catalytic reformer can be satisfactorily operated at low temperature conditions of 1,450°–1,750° F. and at 200–400 psig pressure, its preferred operating conditions are usually 1500°–1700° F. and 300–350 psig pressure.

DESCRIPTION OF THE PREFERRED EMBODIMENT

Figure 1:
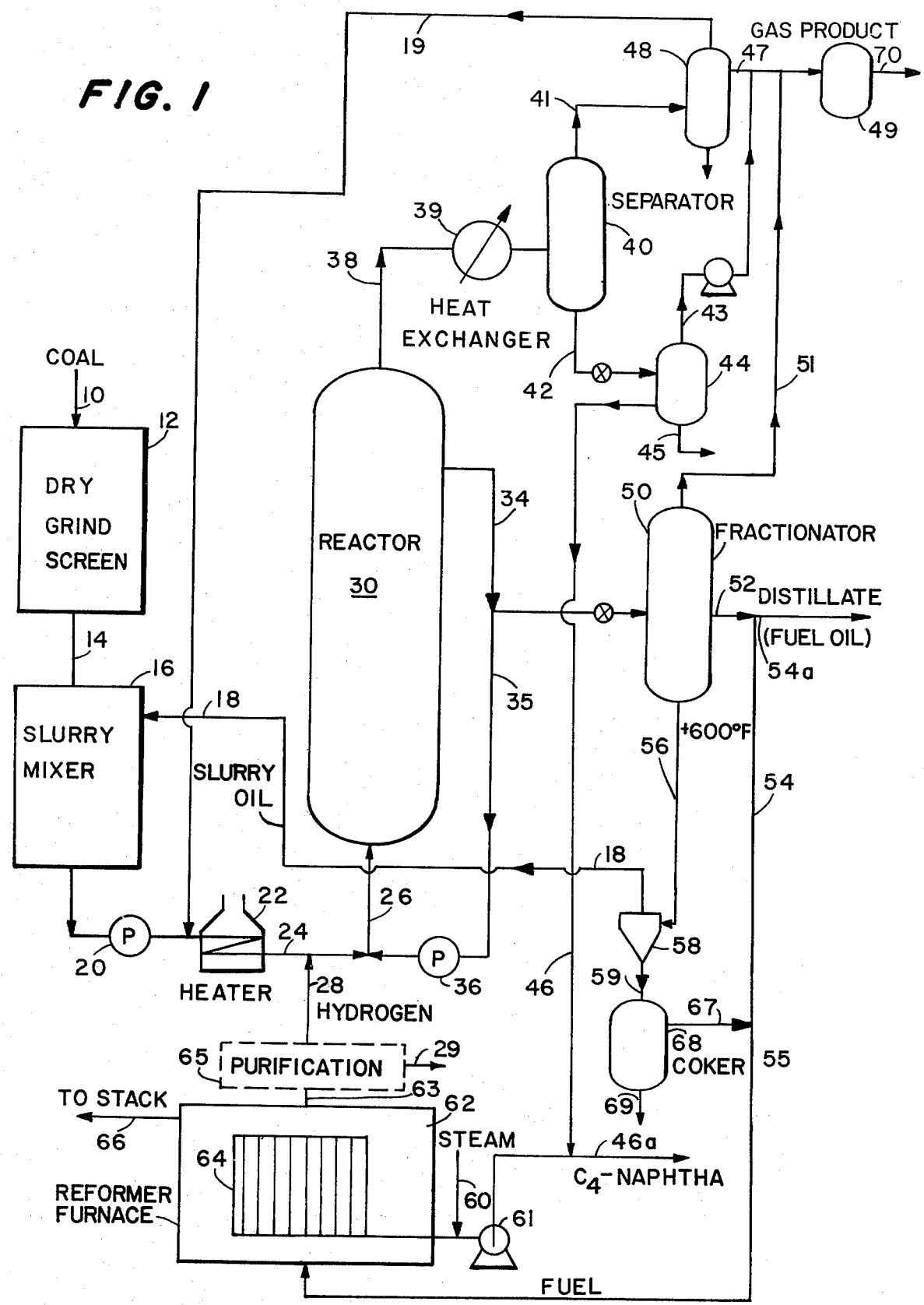
FIG. 1 is a schematic view of the essential process steps for the conversion of coal by hydrogenation to produce mainly fuel gas product.

As shown in FIG. 1, a coal such as bituminous, semi-bituminous, sub-bituminous coals or lignite, entering the system at 10 is first passed through a preparation unit generally indicated at 12. In such a unit it is desirable to dry the coal of surface moisture and to grind the coal to a desired mesh size and then to screen it for uniformity. It is preferable that the coal has a fineness of about 20 mesh (U.S. Sieve Series), but it need not be closely sized beyond avoiding excessive expense in pulverization. However, it will be observed that the preciseness of size may vary between different types of coals and lignite.

The coal fines discharge at 14 into slurry preparation tank 16 where the coal is blended with a slurrying oil indicated at 18 which, as hereinafter pointed out, is conveniently made in the system. To establish an effective transportable slurry, it is found that the ground coal should be mixed with at least about an equal weight of oil and usually not more than one part of coal per eight parts of liquid.

The coal-oil slurry is then pumped at 20 through heater 22 to bring the slurry up to a temperature in the order of 600°–800° F., but preferably 650°–750° F. Hydrogen recovered from scrubber 48 is recycled via line 19 to mix with the coal-oil slurry feed before it enters heater 22. Such heated slurry then discharges at 24 into the reactor feed line 26, wherein it is supplied with make-up hydrogen from line 28, which may be preheated to 900°–1200° F. in accordance with reactor heat balance requirements.

The entire mixture of hydrogen and coal-oil slurry then enters reactor 30, passing upwardly from the bottom at a rate, under pressure, and at a temperature to accomplish the desired hydrogenation. A contact material may be used in the reaction zone, but it is preferable to operate the thermal hydrogenation without a contact material using only the ash solids derived from the coal feed and without added catalyst.

If contact particles are introduced into reactor 30 or ash accumulates, the process takes on the characteristics of an ebullated bed reaction process. The operation of the ebullated bed reactor is disclosed in U.S. Pat. No. 3,617,465 to Wolk et al, which description is incorporated by reference to the extent needed. However, because the process described herein is directed principally to the production of fuel gases instead of liquid products, it is not necessary to promote the catalytic reactions which result in liquids, but rather is preferable to encourage the thermal cracking reactions which produce light gases. This requires operating without added catalyst and maintaining the total solids concentration in the reactor within a controlled range of 8–15 weight percent, of which the ash concentration is usually in the range of 4–7 weight percent.

Preferred reactor operating conditions are in the range of 840°–900° F. temperature and 1200–2800 psig hydrogen partial pressure, most preferably about 850°–880° F. and 1600–2800 psig. Coal throughput is at the rate of 10–15 pounds per hour per cubic foot of reactor space, and preferably 12–40 lb/hr/ft$^3$ reactor space, and hydrogen consumption is about 10–16 SCF/pound coal, so that the yield of unreacted coal is 4 to 8 weight percent of the quantity of moisture and ash free coal feed. The size of the coal and the velocity in the hydrogenation reactor is such that the unreacted coal (char) and ash is carried out with the reaction liquid products at 34. A recycle liquid via stream 35, pump 36, and line 26 may be used to control temperature and promote suspension of solids and turbulence in reactor 30.

The effluent vapor stream 38 is usually cooled at 39 and is passed to phase separator 40. This stream 38 includes principally gaseous fractions and is virtually free of solid particles. Although removal of separate gaseous and liquid streams from reactor 30 is shown, it should be understood that a combined effluent stream can be removed and then phase separated into gas stream 38 and liquid stream 34. From separator 40, a gas stream is removed at 41 and constitutes a portion of hydrocarbon gas product, which is then treated at scrubber 48 to remove a hydrogen component stream which is recycled for reuse in the reactor via line 19. The remaining $C_1$–$C_3$ gas fraction is removed as product gas at 47. Such hydrogen purification at 48 permits a higher purity hydrogen gas to be recycled at 19 to the hydrogenation reactor 30, thus requiring less make-up hydrogen to be produced at reformer 62 by reforming $C_4$–400° F. naphtha stream 46, and also requires less distillate at 55 as fuel for the reformer, as will be described in greater detail below.

A liquid stream 42 is also removed from phase separator 40 and passed to lower pressure separator 44, from which a gaseous fraction 43 is removed and provides another portion of the fuel gas product at 47. Thus, the naphtha stabilization step provided at 44 removes additional dissolved light hydrocarbons from the naphtha stream 42 for gas stream 43, before the remaining naphtha stream 46 is fed to reformer 62. Also, a liquid fraction is removed at 45, which comprises water, ammonia and dissolved $H_2S$. The resulting purified and stabilized naphtha liquid fraction stream 46 has the approximate boiling range and composition of a $C_4$-naphtha fraction, boiling up to about 400° F.

The net slurry effluent stream 34 from reactor 30 is pressure reduced and passed to fractionator 50 for separation into gases and liquid hydrocarbon fractions. A gaseous stream is withdrawn at 51, and combined with streams 43 and 47 to form the plant gas product 70, which is purified of hydrogen sulfide in purification step 49. From fractionator 50 a light distillate liquid fraction is removed at 52 having a boiling range of about 400° F. to 600° F., and a heavy bottoms liquid fraction boiling above 600° F. is removed at 56. Stream 56 is passed to a solids separation step at 58, which is preferably a hydroclone unit although a centrifuge or filter could be used, for removal of sufficient ash and unreacted coal solids to limit the percent solids returned to the reactor in stream 18 and thereby help control the reaction which occurs therein. The reduced-solids overflow liquid stream 18 is returned as slurrying oil to coal-oil mixing step 16, and the remaining underflow 59 containing increased solids concentration is passed to a coking step 68. From such coking step, additional distillate oil usually 600°–975° F. boiling range is recovered at 67 and coke residue is removed at 69.

With coal conversion conditions in reactor 30 maintained within the temperature range of 840° F.–900° F., hydrogen partial pressures from 1200 to about 3000 psig, with coal throughput rates of 10–50 pounds per hour per cubic foot of reaction space, and with recycle of a portion of bottoms fractions 56 as part of the slurry oil 18, the reaction products will be in the order of 18–40 weight percent, preferably 18–35 weight percent, of $C_1$ to $C_3$ gases recovered as streams 47, 43, and 51, a similar amount of $C_4$–400° F. naphtha at 46, and 400°–975° F. distillate or fuel oil fractions 52 and 67, all based on coal feed.

As shown in FIG. 1, a major part of the $C_4$-naphtha stream 46 is pressurized at 61 to 200–400 psig and, together with pressurized steam at 60, is used as feed to the hydrogen reformer furnace 62 by direct introduction into the tubes 64. The reformer furnace tubes 64 are provided with a suitable catalyst as is well understood in the industry, and they will be heated to the preferred temperature range of only about 1500°–1700° F. for the steam reforming step, from which a hydrogen-methane gas stream is produced. A portion 54 of the coal liquid fraction 52, and distillate 67 from the coker 68 are used as fuel 55 for direct heating of the reformer tubes 64. A stack gas is removed at 66. Some purification of the effluent gas stream 63 from the reformer 62 is usually necessary, such as in purification unit 65, with a high yield of make-up hydrogen being provided at 28. Impurities such as $CO_2$ can be removed at 29.

If desired due to reduced seasonal gas product demands, portions of $C_4$–400° F. liquid fraction 46 can be withdrawn as product at 46a and 400°–600° F. fraction distillate liquid product can be withdrawn at 54a as product.

The process of the invention is further illustrated by the following representative examples, which are not to be construed as limiting the scope of this invention.

EXAMPLE 1

Hydrogenation operations without added catalyst were conducted on a Pittsburgh Seam coal at various reaction conditions to produce $C_1$–$C_3$ fuel gas along with various liquid fraction products. Analysis of the coal feed is given in Table 1 below. A summary of results is shown in Table 2.

TABLE 1
ANALYSIS FOR PITTSBURGH SEAM COAL
Coal Analyses, W %

| | |
|---|---|
| Moisture | 1.93 |
| Ash (Dry Basis) | 8.60 |
| Volatile Matter (Dry Basis) | 42.46 |
| Fixed Carbon (Dry Basis) | 48.95 |
| Carbon (Dry Basis) | 73.92 |
| Hydrogen | 5.24 |
| Nitrogen | 1.30 |
| Sulfur | 4.40 |
| Ash | 8.60 |
| Oxygen | 6.81 |

TABLE 2
HYDROGENATION OF PITTSBURGH SEAM COAL

| Run No. | 1 | 2 | 3 | 4 | 5 |
|---|---|---|---|---|---|
| Coal Rate, Lbs/Hr/Ft³ Reactor | 31.2 | 31.2 | 31.2 | 93.7 | 93.7 |
| Slurry Oil Rate, Lbs/Lb Coal | 4.41 | 4.08 | 4.0 | 4.06 | 4.08 |
| Slurry Oil | | | | | |
| Initial Boiling Point, °F. | ← | ← | 356 | → | → |
| End Point, °F. | | | 836 | | |
| Hydrogen Content, W % | | | 7.35 | | |
| H₂ Partial Pressure, psig | 2250 | 2250 | 2250 | 2250 | 2250 |
| Reactor Temperature, °F. | 850 | 893 | 920 | 850 | 893 |
| Yields, W % of Dry Coal | | | | | |
| C₁—C₃ Hydrocarbon Gases | 4.5 | 10.1 | 17.5 | 2.2 | 4.8 |
| C₄–400° F. Liquids | 3.1 | 5.6 | 3.1 | 3.1 | 3.4 |
| 400°–975° F. Liquids* | 25.6 | 30.2 | 23.2 | 15.1 | 23.6 |
| 975° F. + Residual Oils | 49.4 | 39.2 | 39.6 | 60.4 | 48.9 |
| Unconverted Coal | 5.9 | 5.1 | 4.2 | 7.6 | 6.0 |
| Ash | 7.7 | 7.7 | 7.6 | 7.8 | 8.2 |
| H₂O | 0.3 | 0.0 | 0.0 | 0.6 | 1.6 |
| CO₂ | 0.6 | 0.5 | 0.6 | 0.4 | 0.5 |
| NH₃ | 1.2 | 1.5 | 1.5 | 1.0 | 1.2 |
| H₂S | 3.3 | 1.8 | 3.9 | 2.5 | 3.3 |
| Total | 101.6 | 101.7 | 101.2 | 100.7 | 100.6 |
| Hydrogen Reacted, W % of Dry Coal | 1.6 | 1.7 | 1.2 | 0.7 | 0.6 |

*Net after meeting slurry oil requirement

Table 2 shows the effect of reaction temperature and coal feed rates on the thermal conversion of coal to produce high heating value gas (approximately 1000 Btu/ft³). In these runs the slurry oil composition returned to the reactor was the same for each. As can be seen, the $C_1$–$C_3$ light gas yield was increased several fold by increasing the reaction temperature from 850° F. to 920° F. (Runs 1 and 3) at the same coal feed rate, while the yields of the fuel oil (400°–975° F.) and residual oil (975° F.+) fractions declined. Substantially the same product yield patterns for Run 1 was obtained at the higher coal feed rate by also using higher reaction temperatures, such as shown by the three-fold increase in feed rate giving equivalent yield results when the reaction temperature was increased to 893° F. (Runs 1 and 5). However, the yields of $C_1$–$C_3$ gas and $C_4$–400° F. naphtha liquid were less than desired.

EXAMPLE 2

A further run (No. 6) was made on Pittsburgh Seam coal at the same reaction temperature and pressure as for Run 1, but at lower feed rate (18.7 lb/hr/ft³) while recycling oil containing a high proportion boiling above 975° F. to determine the effect upon production of $C_1$–$C_3$ gas and liquid fractions. Results are presented in Table 3, and show a substantial desirable increase in both $C_1$–$C_3$ gas production and $C_4$–400° F. liquid production, and a corresponding decline in residual oil product fraction, while the 400°–975° F. distillate fraction remained essentially unchanged, as compared to the Table 2 results.

TABLE 3

HYDROGENATION OF PITTSBURGH SEAM COAL TO PRODUCE FUEL GAS

| Run No. | 6 | 7 |
|---|---|---|
| Reactor Conditions | | |
| Temperature, °F. | 850 | 875 |
| $H_2$ Partial Pressure, psig | 2250 | 2250 |
| Coal Feed Rate, Lbs/Hr/Ft$^3$ | 18.7 | 18.7 |
| Hydrogen Recycle Rate, SCF/Lb Coal | 25 | 25 |
| Recycle Slurry Oil, Lb Oil/Lb Coal | 1.4 | 1.4 |
| (56 W % Boiling 400° F. to 975° F., | | |
| 44 W % Boiling above 975° F.) | | |
| Yields from Liquid Phase Conversion, W % | | |
| $C_1$—$C_3$ Hydrocarbons | 21.7 | 28.4 |
| $C_4$-400° F. Liquids | 25.2 | 31.4 |
| 400°–975° F. Liquids | 25.8 | 14.5 |
| 975° F. + Residue | 12.2 | 7.0 |
| Hydrogen Plant Requirements, SCF/Lb Coal | | |
| Hydrogen Consumed in Liquid Phase Conversion | 11.8 | 14.6 |
| Unconsumed Hydrogen included in Fuel Gas Product | 2.5 | 3.2 |
| Hydrogen Production | 14.3 | 17.8 |
| Feed to Hydrogen Plant, Lb/Lb Coal | | |
| $C_4$-Naptha (46) | 0.172 | 0.314 |
| Distillates to Fire Reformer Furnace (55) | 0.159 | 0.215 |
| Net Plant Production, SCF/Lb Coal | | |
| Unconsumed Hydrogen (47) | 2.50 | 3.20 |
| $C_1$—$C_3$ Hydrocarbons (43 & 51) | 3.20 | 6.05 |
| Total Gas (1000 Btu/SCF) (70) | 5.70 | 9.25 |
| Naphtha, Lb/Lb Coal (46) | 0.080 | 0.000 |
| Fuel Oil (Less than 0.45 W % Sulfur), Lb/Lb Coal (52 & 67) | 0.221 | 0.000 |

In operations with the same coal feed rate and pressure but with the reactor temperature increased to 875° F., the product distribution from the conversion reaction can be altered as projected for Run 7 of Table 3. It is seen that $C_1$-$C_3$ gas and light $C_4$-400° F. liquid production are increased further, while the production of both the 400°–975° F. heavy liquid and 975° F.+ residual liquid fractions are decreased correspondingly. The hydrogen consumption in the liquid phase conversion is also increased to 14.6 SCF/lb coal. For Run 7, all of the $C_4$-400° F. light hydrocarbon liquids from stream 46 can be fed to steam reformer 62 to produce 17.8 SCF of hydrogen in a gas mixture comprising 90.8% purity hydrogen and 9.2% $CH_4$, while consuming all of the heavier 400°–975° F. liquids from streams 52 and 67 as fuel for the reformer. The net plant product then becomes about 9.25 SCF of 1000 Btu/ft$^3$ heating value gas per pound of coal at 47, 43, and 51, representing about 68.5 percent of the heating value of the original coal.

EXAMPLE 3

Further hydrogenation operations without added catalyst were conducted to confirm the results of Example 2 on Pittsburgh Seam coal at both lower feed rate (12.5 lb/hr/ft$^3$) and slightly lower hydrogen partial pressures than 2250 psig. Results are presented in Table 4 and are also plotted as FIG. 2 for 12.5 lb/hr/ft$^3$ feed rate.

TABLE 4

HYDROGENATION OF PITTSBURGH SEAM COAL AT LOWER FEED RATES

| | A | B | C | D | E |
|---|---|---|---|---|---|
| Reactor Conditions | | | | | |
| Temperature, °F. | 850 | 850 | 860 | 870 | 880 |
| $H_2$ Partial Pressure, psig | 1850 | 1780 | 2000 | 2150 | 2100 |
| Coal Rate, Lb/Hr/Ft$^3$ | 18.7 | 12.5 | 12.5 | 12.5 | 12.5 |
| Recycle Slurry Oil*, Lb Oil/Lb Coal | 5.0 | 7.0 | 7.0 | 7.0 | 7.0 |
| Yields, W % Dry Coal | | | | | |
| $C_1$—$C_3$ Gases | 14.55 | 20.28 | 21.48 | 22.97 | 27.49 |
| $C_4$-400° F. Liquids | 21.21 | 26.71 | 25.68 | 30.64 | 33.37 |
| 400°–975° F. Liquids | 33.48 | 31.79 | 28.05 | 25.38 | 18.99 |
| 975° F. + Residue | 14.76 | 5.37 | 8.69 | 6.45 | 3.63 |
| Unreacted Coal | 4.17 | 4.04 | 3.62 | 3.38 | 3.86 |
| Ash, W % | 8.55 | 8.24 | 8.23 | 7.52 | 8.28 |
| $H_2$ Consumption | 5.30 | 6.96 | 6.76 | 7.30 | 8.18 |

*Composition of slurry oil was
66% boiling 400° F.–975° F.
26% boiling above 975° F.
8% solids Similar to Example 2 results, it is seen that at a particular coal feed rate the fractions of $C_1$-$C_3$ gas product and $C_4$-400 liquid product increase with increasing reactor temperature, between 850° and 880° F., while the 400°–975° F. liquid fraction decreases substantially. Also as the coal feed rate or reactor space velocity is increased, both the $C_1$-$C_3$ gas fraction and the $C_4$-400° F. liquid fraction are correspondingly reduced, while the 400°–975° F. and the 975° F.+ liquid fractions are increased (Condition A).

Thus for the higher severity reaction conditions of about 865°–880° F. and 10–15 lb/hr/ft$^3$ coal feed rate increased $C_1$-$C_3$ fuel gas is produced, whereas for lower severity reaction conditions of 840°–865° F. and 15–30 lb/hr/ft$^3$ feed rate, the production of $C_1$-$C_3$ gas decreases and some increase in the heavy liquid products occurs. For all cases, sufficient $C_4$-400° F. naphtha fraction is made to be used as feed to the reformer to produce the hydrogen needed in the hydrogenation reaction step.

The hydrogenation results of Case E in Table 4 permit the production of about 38 weight percent of $C_1$-$C_3$ fuel gas as the sole product of the integrated process operation. The entire $C_4$-400° F. naphtha product is taken to steam reforming and the 400° F.–975° F. distillates from the hydrogenation operation are used for fuel for steam reforming and other plant fuel requirements. The naphtha will provide hydrogen equal to 9.78 weight percent of coal, and methane equal to 8.48 weight percent of coal. The net plant product will then be (as W % of dry coal):

| | |
|---|---|
| $C_1$—$C_3$ from Coal Hydrogenation | 27.49 |
| Methane from Naphtha Reforming | 8.48 |
| Hydrogen Unconsumed in Process | 1.60 |
| Plant Gas Product | 37.57 |

The combined gases will have a heating value of 1,000 Btu/SCF, and amount to 9.24 SCF/pound coal fed to process, and have a fuel value equal to 68.7% of that of the coal fed to the process.

Figure 2:
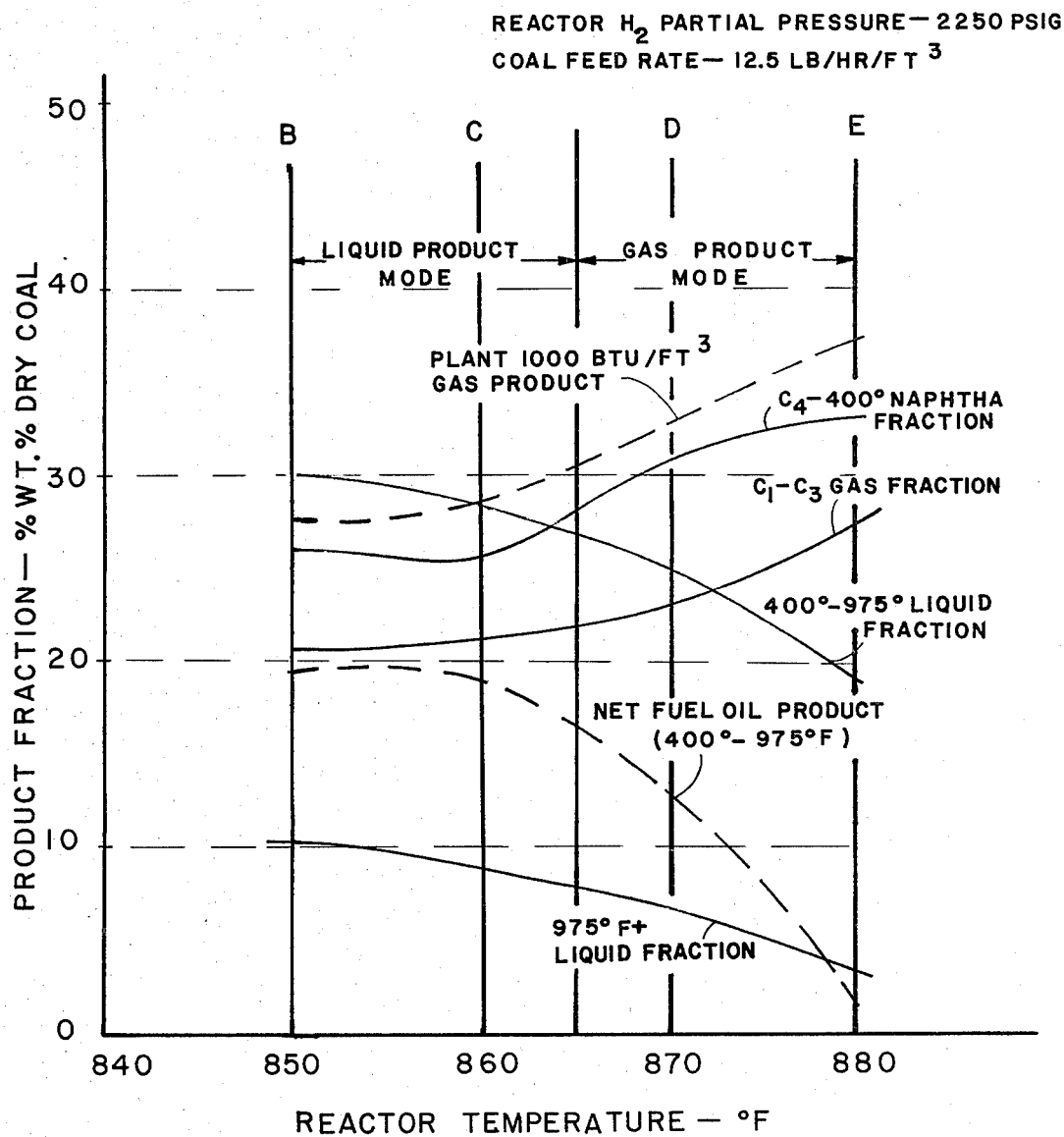
FIG. 2 is a graph showing the various coal product fractions produced plotted against hydrogenation reaction temperature, and the net product yields after meeting the hydrogen and fuel requirements of the process.

FIG. 2 shows the interrelation of the hydrogenation yields of Table 4, and the plant yield of 1000 Btu gas and fuel oil. By reducing the hydrogenation reaction severity from 880° F. to 850°–860° F, the plant yield of 1000 Btu/SCF gas is lowered to about 28 weight percent of dry coal, having 51% of the fuel value of coal fed, while making available a fuel oil (400°–600° F.) as plant product amounting to 19 weight percent of the coal fed and having a fuel value of 24% of that of the coal fed.

As disclosed in the foregoing, this coal hydrogenation process without added catalyst produces a maximum of fuel gas while providing the hydrocarbons required to feed and operate the steam reformer to produce the hydrogen consumed in the conversion of the coal. It is evident that other combinations of feed rate, reactor temperature, and pressure can be used to obtain selectivity for the light gas, naphtha, and fuel oil necessary to fulfill the chemical and fuel requirements of the integrated hydrogen plant, and the exact selection of conditions depends upon economic considerations of optimum cost and desired net production distribution.

Although certain specific embodiments of the invention have been described and shown, it is to be understood that they are meant to be illustrative only and not limiting in scope and that some features may be changed without departing from the spirit or essence of the invention. It is apparent that the present invention has broad application to the thermal hydroconversion of coal to produce substantially fuel gas product. Accordingly, the invention is not to be construed as limited to the specific embodiments illustrated but only as defined by the following claims.

I claim:

1. A process for the principal production of a methane through propane fuel gas product from coal, wherein the coal is subjected to a liquid-phase thermal hydroconversion reaction without added catalyst, comprising the steps of:
   (a) slurrying the coal with a heavy hydrocarbon liquid made in the process and feeding said slurry to the reaction zone;
   (b) feeding hydrogen to said reaction zone;
   (c) operating said reaction zone at a temperature between 840° F. and 920° F. and at a hydrogen partial pressure between 1000 and 3000 psig;
   (d) maintaining a coal throughput rate of 5–50 pounds per hour per cubic foot of reaction space;
   (e) removing gaseous and liquid effluent streams from said reaction zone;
   (f) separating from said gaseous effluent stream a $C_4$-naphtha fraction;
   (g) passing a major portion of said $C_4$-naphtha fraction from (f) and steam as feed to a catalytic steam reformer producing hydrogen which is fed to (b);
   (h) passing a major portion of said liquid stream from (e) to said steam reformer as fuel for heating said reformer to 1450°–1750° F. temperature; and
   (i) recovering from said gaseous stream in (f) the fuel gas product comprising 14–40 weight percent of the coal feed.

2. The process of claim 1 wherein said liquid stream in (e) is separated into a $C_1$–$C_3$ gas product fraction, a 400°–600° F. distillate liquid fraction, and a 600° F.+ bottoms liquid fraction.

3. The process of claim 1 wherein said effluent gaseous stream in (e) is further separated into said $C_4$-naphtha fraction, medium purity hydrogen and fuel gas product.

4. The process of claim 1 wherein said hydrogen produced in (g) is a hydrogen-methane mixture which is provided to said reaction zone in (b).

5. The process of claim 2 wherein said hydrocarbon slurrying liquid in (a) is a reduced solids portion of said bottoms fraction.

6. The process of claim 2 wherein a major portion of said distillate fraction is used in (h) as fuel for the direct heating of said reformer, and the remainder is withdrawn as liquid product.

7. The process of claim 2 wherein a portion of the bottoms liquid fraction having increased solids content is passed to a coking step from which a light liquid fraction is recovered as additional fuel for said reformer.

8. The process of claim 1 wherein the coal is Pittsburgh Seam coal, said reaction zone temperature is 840°–900° F., hydrogen partial pressure is 1600–2800 psig, coal throughput rate is 10–40 lb/hr/ft$^3$.

9. The process of claim 1 wherein the gaseous effluent stream in (e) is also separated at (f) into a medium purity hydrogen gas which is recycled to the reaction zone.

10. The process of claim 3 wherein the $C_4$-naphtha fraction is further phase separated at lower pressure, and additional light gas fraction is recovered and combined with the fuel gas product.

11. The process of claim 1 wherein the steam reforming conditions at (h) are 1500°–1700° F. temperature and 200–400 psig pressure.

12. The process of claim 2 wherein the total fuel gas product comprises 35–40 weight percent of coal feed, all the $C_4$-naphtha fraction produced is used as feed to the reformer to produce hydrogen, and all the distillate liquid fraction is used as fuel to the reformer.

13. The process of claim 2 wherein the fuel gas product comprises 18–35 weight percent of coal feed, all the $C_4$-naphtha fraction is used as feed to the reformer to produce hydrogen, and a minor portion of the distillate liquid fraction not needed for fuel to the reformer is withdrawn as net liquid product.

14. A process for the principal production of a methane through propane fuel gas product from Pittsburgh Seam coal, wherein the coal is subjected to a liquid-phase thermal hydroconversion reaction without added catalyst comprising the steps of:
   (a) slurrying the coal with a heavy hydrocarbon liquid made in the process and feeding said slurry to the reaction zone;
   (b) feeding hydrogen to said reaction zone;
   (c) operating said reaction zone at a temperature between 840° F. and 900° F. and at a hydrogen partial pressure between 1600 and 2800 psig; said reaction zone having a solids content of 8–15 wt. % comprising 4–7 wt. % ash;
   (d) maintaining a coal throughput rate of 10–40 pounds per hour per cubic foot of reaction space;
   (e) removing gaseous and liquid effluent streams from said reaction zone;
   (f) separating from said gaseous effluent stream a medium purity hydrogen stream, a gas product fraction, and a $C_4$ naphtha fraction, and said liquid effluent stream is separated into a 400°–600° F. distillate liquid fraction, and a 600° F. plus bottoms liquid fraction;
   (g) passing a major portion of said $C_4$-naphtha fraction from (f) with steam as feed to a catalytic steam reformer producing hydrogen which is fed to (b);
   (h) passing a major portion of said liquid 400°–600° F. fraction from (f) to said steam reformer as fuel for heating of said reformer to 1450°–1750° F. temperature; and
   (i) recovering from said gaseous stream in (f) the fuel gas product comprising 10–40 weight percent of the coal feed, 15. The process of claim 14 wherein the 600° F. plus liquid fraction from (f) is separated into a reduced solids liquid stream which recycled as slurrying oil in (a), an increased solids stream is passed to a coking step from which a light liquid fraction is recovered as additional fuel for said reformer, and the reformer temperature is 1500°–1700° F.

16. A process for the principal production of a methane through propane fuel gas product from coal, wherein the coal is subjected to a liquid-phase thermal hydroconversion reaction without added catalyst, comprising the steps of:
 (a) slurrying the coal with a heavy hydrocarbon liquid made in the process and feeding said slurry to the reaction zone;
 (b) feeding hydrogen to said reaction zone;
 (c) operating said reaction zone at a temperature between 840° F. and 920° F. and at a hydrogen partial pressure between 1000 and 3000 psig;
 (d) maintaining a coal throughput rate of 5–50 pounds per hour per cubic foot of reaction space;
 (e) removing vapor and liquid effluent from said reaction zone;
 (f) separating said effluent into a gaseous fraction comprising hydrogen and $C_1$–$C_3$ hydrocarbons, a $C_4$–naphtha fraction and at least one fraction with components boiling between 400° F. and 975° F.;
 (g) passing a major portion of said $C_4$–naphtha fraction and steam as feed to a catalytic steam reformer producing hydrogen which is fed to (b);
 (h) passing a major portion of said 400°–975° F. fraction to said steam reformer as fuel for heating said reformer to 1450°–1750° F. temperature; and
 (i) recovering major amounts of $C_1$–$C_3$ gaseous product and optionally minor amounts of liquid product boiling between 400° and 975° F., said gaseous product being recovered in amounts between 14–40 weight percent based upon the coal feed, and said liquid being recovered in amounts between 0–20 weight percent based upon the coal feed.

17. The process of claim 1, wherein the reaction zone is maintained under conditions of 865°–880° F., 1750–2800 psig (hydrogen partial pressure), and the space velocity (coal throughput) is between 10–30 pounds coal per hour per cubic foot of reactor space.

18. The process of claim 1, wherein the reactor zone is maintained under conditions 850°–865° F., 1700–2600 psig (hydrogen partial pressure) and the space velocity (coal throughput) is 15 to 40 pounds per hour per cubic foot of reactor space.

19. The process of claim 17 or claim 18, wherein the vapor and liquid are removed in a single stream and the separation of step (f) comprises the step of:
 (1) phase separating said single stream into a vaporous stream and a liquid stream;
 (2) passing said vaporous stream of reduced temperature to a separator to produce an overhead gaseous stream comprising hydrogen and $C_1$ to $C_3$ hydrocarbons, and an underflow stream comprising $C_4$ to naphtha hydrocarbons;
 (3) passing said liquid stream to a fractionator to produce a $C_1$–$C_3$ overhead stream a 400°–600° F. light distillate stream, and 600° F.+ underflow stream containing solids of unreacted coal and ash; and
 (4) passing said 600° F.+ underflow stream to a solids separator to produce a solids reduced overflow and a solids increased underflow.

20. The process of claim 19, wherein the solids reduced underflow is passed to a coking step to produce 600°–975° F. distillate stream.

21. The process of claim 19, wherein the said solids reduced overflow is utilized as the heavy hydrocarbon to slurry with the coal.

22. The process of claim 20, wherein said solids reduced overflow is utilized as the heavy hydrocarbon to slurry with the coal.

* * * * *